United States Patent [19]

Hasegawa et al.

[11] 4,122,178

[45] Oct. 24, 1978

[54] PIPERAZINE COMPOUNDS

[75] Inventors: Gen Hasegawa, Tokyo; Takanori Oe, Oita; Chiaki Kitami, Fukuoka, all of Japan

[73] Assignee: Yoshitomi Pharmaceutical Industries, Ltd., Osaka, Japan

[21] Appl. No.: 692,395

[22] Filed: Jun. 3, 1976

[30] Foreign Application Priority Data

Jun. 3, 1975 [JP] Japan .................................. 50-67324

[51] Int. Cl.$^2$ .......................................... C07D 295/04
[52] U.S. Cl. .................................... 424/250; 544/392; 544/394; 544/398
[58] Field of Search ................... 260/268 R, 268 PH; 424/250

[56] References Cited

U.S. PATENT DOCUMENTS

| | | | |
|---|---|---|---|
| 2,952,681 | 9/1960 | Dudson | 260/268 |
| 3,840,529 | 10/1974 | Maruyama et al. | 260/240 H |
| 3,845,057 | 10/1974 | Maruyama et al. | 260/268 PH |
| 3,923,794 | 12/1975 | Maruyama et al. | 260/268 PH |
| 3,957,788 | 5/1976 | Nishimura et al. | 260/243 C |
| 3,969,356 | 7/1976 | Milkowski et al. | 260/243 C |
| 3,988,456 | 10/1976 | Mishimura et al. | 260/268 PH |

OTHER PUBLICATIONS

Chem. Abstracts, vol. 76, 72557(d) 1972, Abstracting Ger. Offen. 2,125,037.

*Primary Examiner*—Nicholas S. Rizzo
*Attorney, Agent, or Firm*—Sughrue, Rothwell, Mion, Zinn and Macpeak

[57] ABSTRACT

Piperazine compounds useful as analgesics, and having the formula:

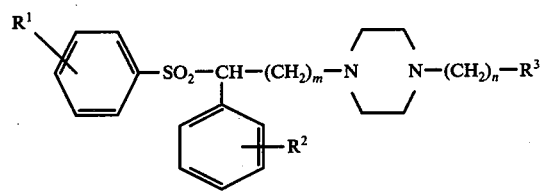

wherein each of $R^1$ and $R^2$ is hydrogen, halogen, $C_{1-4}$ alkyl, $C_{1-4}$ alkoxy or $CF_3$; $R^3$ is hydrogen, hydroxyl, an optionally substituted phenyl (e.g. phenyl, halo-phenyl, $C_{1-4}$ alkyl-phenyl, $C_{1-4}$ alkoxy-phenyl or $CF_3$-phenyl), pyridyl, 2-thienyl or 2-pyrimidinyl; $m$ is 2 or 3; and $n$ is 0, 1 or 2, and pharmaceutically acceptable acid addition salts thereof are disclosed.

12 Claims, No Drawings

PIPERAZINE COMPOUNDS

The present invention relates to novel and therapeutically valuable piperazine compounds of the formula:

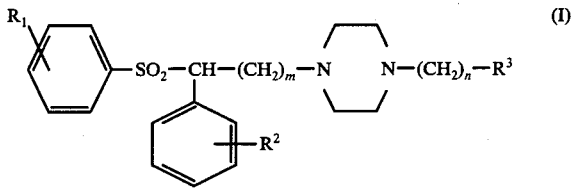

and pharmaceutically acceptable acid addition salts thereof, wherein:

each of $R^1$ and $R^2$ is a hydrogen atom, a halogen atom, (e.g. Cl, Br or F), an alkyl group having 1 to 4 carbon atoms (e.g. methyl, ethyl, propyl, isopropyl or butyl), an alkoxy group having 1 to 4 carbon atoms (e.g. methoxy or ethoxy) or a trifluoromethyl group;

$R^3$ is a hydrogen atom, a hydroxyl group, an optionally substituted phenyl group (e.g. phenyl, halophenyl, lower alkyl-phenyl, lower alkoxy-phenyl or trifluoromethyl-phenyl), pyridyl, 2-thienyl or 2-pyrimidinyl;

m is 2 or 3; and n is 0, 1 or 2.

The compounds of formula (I) can be produced by reacting a compound of the formula:

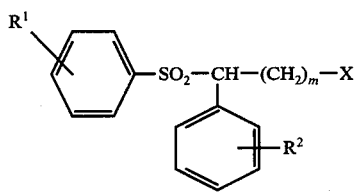

wherein X is an acid residue of reactive ester such as a halogen atom (e.g. Cl or Br), an alkylsulfonyloxy group (e.g. mesyloxy) or an arylsulfonyloxy group (e.g. tosyloxy), and the other symbols are as defined above, with a compound of the formula:

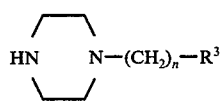

wherein each symbol is as defined above.

The reaction is usually carried out without a solvent or in an inert solvent such as methanol, ethanol, propanol, 2-propanol, butanol, benzene, toluene or dimethylformamide, at a temperature of from room temperature to the boiling point of the solvent employed, for 5 to 72 hours. The reaction is advantageously carried out in the presence of a deacidifying agent such as potassium carbonate, sodium carbonate, potassium hydroxide, sodium hydroxide or triethylamine.

The compounds of the present invention can be converted in a conventional manner into the corresponding acid addition salts with various inorganic or organic acids such as hydrochloric, hydrobromic, sulfuric, maleic, fumaric, oxalic and citric acids.

The present invention provides such novel piperazine compounds as described in the following:

(1) 1-(4-phenyl-4-phenylsulfonylbutyl)-4-phenylpiperazine
(2) 1-(4-phenyl-4-phenylsulfonylbutyl)-4-(o-chlorophenyl)piperazine
(3) 1-(4-phenyl-4-phenylsulfonylbutyl)-4-(m-chlorophenyl)piperazine
(4) 1-(4-phenyl-4-phenylsulfonylbutyl)-4-(p-chlorophenyl)piperazine
(5) 1-(4-phenyl-4-phenylsulfonylbutyl)-4-(m-tolyl)piperazine
(6) 1-(4-phenyl-4-phenylsulfonylbutyl)-4-(p-methoxyphenyl)piperazine
(7) 1-(4-phenyl-4-phenylsulfonylbutyl)-4-(m-trifluoromethylphenyl)piperazine
(8) 1-(4-phenyl-4-phenylsulfonylbutyl)-4-(o-ethylphenyl)piperazine
(9) 1-(4-phenyl-4-phenylsulfonylbutyl)-4-methylpiperazine
(10) 1-(4-phenyl-4-phenylsulfonylbutyl)-4-(2-hydroxyethyl)piperazine
(11) 1-(4-phenyl-4-phenylsulfonylbutyl)-4-(p-chlorobenzyl)piperazine
(12) 1-(4-phenyl-4-phenylsulfonylbutyl)-4-(4-pyridylmethyl)piperazine
(13) 1-(4-phenyl-4-phenylsulfonylbutyl)-4-[2-(4-pyridyl)ethyl]piperazine
(14) 1-(4-phenyl-4-phenylsulfonylbutyl)-4-(2-thienylmethyl)piperazine
(15) 1-(4-phenyl-4-phenylsulfonylbutyl)-4-(2-pyrimidinyl)piperazine
(16) 1-[4-(o-chlorophenyl)-4-phenylsulfonylbutyl]-4-phenylpiperazine
(17) 1-[4-(m-chlorophenyl)-4-phenylsulfonylbutyl]-4-phenylpiperazine
(18) 1-[4-(p-chlorophenyl)-4-phenylsulfonylbutyl]-4-phenylpiperazine
(19) 1-[4-(p-fluorophenyl)-4-phenylsulfonylbutyl]-4-phenylpiperazine
(20) 1-[4-(p-methoxyphenyl)-4-phenylsulfonylbutyl]-4-phenylpiperazine
(21) 1-[4-(p-chlorophenyl)sulfonyl-4-phenylbutyl]-4-phenylpiperazine
(22) 1-(4-phenyl-4-tosylbutyl)-4-phenylpiperazine
(23) 1-[4-phenylsulfonyl-4-(m-trifluoromethylphenyl)-butyl]-4-phenylpiperazine
(24) 1-[4-(p-chlorophenyl)-4-(p-chlorophenyl)sulfonylbutyl]-4-phenylpiperazine
(25) 1-[4-(p-fluorophenyl)sulfonyl-4-(o-tolyl)butyl]-4-(m-chlorophenyl)piperazine
(26) 1-(3-phenyl-3-phenylsulfonylpropyl)-4-(m-chlorophenyl)piperazine
(27) 1-[3-(p-methoxyphenyl)-3-phenylsulfonylpropyl]-4-phenylpiperazine The starting compound of formula (II) wherein, for example, each of $R^1$ and $R^2$ is H, m is 3 and X is Cl can be produced by such a conventional manner as described in the following reaction sheme:

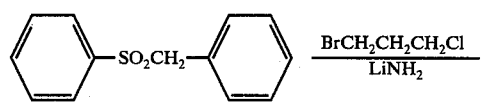

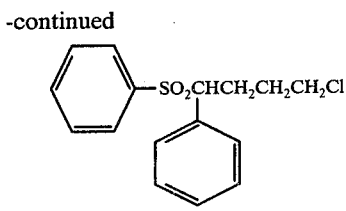

SPECIFIC EXAMPLE OF THE PREPARATION OF COMPOUND (II)

To lithium amide obtained by dissolving 0.84 g of metallic lithium into liquid ammonia was added 23.2 g of phenylmethylsulfonylbenzene. After stirring for 2 hours, 150 ml of toluene was added while the ammonia was distilled off. After refluxing for 30 minutes, the reaction mixture was cooled to 50° C and to the mixture was added dropwise 23 g of 1-bromo-3-chloropropane at 50°-60° C. The whole mixture was left for 2 hours at the same temperature and then refluxed for 40 minutes. The resulting solution was washed with water and dried over magnesium sulfate and then concentrated. The residue was separated by a column chromatography (silica gel; a mixture of n-hexane and chloroform) and purified with ethanol to give 1-chloro-4-phenyl-4-phenylsulfonylbutane, melting at 110°-112° C.

The compounds of formula (I) and pharmaceutically acceptable acid addition salts thereof have weak respiratory depression activity, and non-narcotic analgesic activity as shown, for example, by the following tests:

TESTING METHODS

I. Phenylquinone Method

According to the method of Hendershot et al. described in "Journal of Pharmacology and Experimental Therapeutics", vol. 125, p. 237 ff. (1957), to one group of six dd-strain male mice each weighing about 20 g a test solution containing a test compound was orally administered and one hour later 0.2 ml 20 g of body weight of 0.02% o-phenyl-p-benzoquinone solution was intraperitoneally injected. The frequency of stretch symptoms thus induced was measured for 30 minutes, and compared with that of a control group, and the inhibition percentage (effect) was calculated.

The $ED_{50}$ (50% effective dose) was determined graphically.

II. Tooth Pulp Nociception Method

The tooth pulp threshold changes were measured by a modification of the method of Yim et al. described in "Journal of Pharmacology and Experimental Therapeutics," vol. 115, p. 96 ff. (1955). Briefly, insulated metal (silver) electrodes were attached to holes which were drilled in the rabbit's upper incisors one hour prior to the experiment. Square wave monophasic pulse of 0.1 millisecond duration at a frequency of 25 per second were then delivered from a stimulator (Nihon Koden Stimulator Model MSE-3). The valtage was increased until pain responses which consisted of chewing movements were obtained. Subsequently suprathreshold stimuli were given and the voltage was gradually decreased until no response was obtained and the lowest voltage producing responses was recorded as the threshold. Stimuli were delivered no oftener than every 15 seconds when the threshold was determined. Each experiment consisted of the determination of not less than three control values of tooth pulp threshold. Following control determination, test compounds were administered intravenously via the marginal ear vein. The tooth pulp threshold was then made 15 minute intervals for 90 minutes and subsequently at 30 minute intervals for a total of 240 minutes.

Analgesic activity was determined according to the following formula:

$$\text{Analgesic activity (\%)} = \frac{b - a}{a} \times 100$$

wherein $a$ is mean threshold voltage of normal and $b$ is maximum threshold voltage of test.

RESULTS

Table I

| | $ED_{50}$ (mg/kg) | |
|---|---|---|
| Compounds | Phenylquinone (p.o.) | Tooth Pulp Nociception (i.v.) |
| A | 3 | 2.5 |
| B | 6 | 5 |
| C | 4.5 | 5 |
| D | 3 | ≦5 |

Compounds A to D are identified below:

A: 1-(4-phenyl-4-phenylsulfonylbutyl)-4-phenylpiperazine oxalate

B: 1-(4-phenyl-4-phenylsulfonylbutyl)-4-(m-chlorophenyl)piperazine dihydrochloride C: 1-(4-phenyl-4-phenylsulfonylbutyl)-4-(m-chlorophenyl)piperazine oxalate D: 1-(4-phenyl-4-phenylsulfonylbutyl)-4-(m-tolyl)piperazine oxalate In view of various tests including these mentioned above, the compounds of formula (I) and pharmaceutically acceptable acid addition salts thereof can be administered safely as analgesics, either alone or in the form of a pharmaceutical composition consisting essentially of a therapeutically effective amount of the compound in admixture with a suitable and conventional carrier or adjuvant, administrable orally or by way of injection, without harm to the host.

The pharmaceutical composition can take the form of tablets, granules, powder or capsules, for oral administration, of injectable solution for subcutaneous or intramuscular administration, or suppository for topical administration. The choice of carrier is determined by the preferred form of administration, the solubility of the compounds and standard pharmaceutical practice.

FORMULATION EXAMPLES (a) 50 mg tablets are prepared from the following composition:

| 1-(4-phenyl-4-phenylsulfonylbutyl)-4-phenylpiperazine oxalate | | |
|---|---|---|
| | 50 | mg |
| Lactose | 88.2 | |
| Corn Starch | 30 | |
| Crystalline Cellulose | 10 | |
| Methyl Cellulose | 0.8 | |
| Magnesium Stearate | 1 | |
| | 180 | mg |

The tablets may be sugar-coated in a conventional manner.

(b) 15 mg injections are prepared from the following composition:

| | |
|---|---|
| 1-(4-phenyl-4-phenylsulfonylbutyl)-<br>-4-(m-chlorophenyl)piperazine<br>dihydrochloride | 15 mg |
| Propylene Glycol | 200 mg |
| Glucose for Injection | 50 mg |
| Water for Injection | a sufficient quantity<br>to make 1 ml. |

The daily dose of compound (I) or a salt thereof for human adults usually ranges from 150 to 300 mg for oral administration and from 90 to 240 mg for subcutaneous, intravenous or intramuscular administration, but it may vary depending upon the age, body weight, and/or severity of the conditions to be treated as well as the response to the medication.

The present invention is further explained by way of the following illustrative examples:

EXAMPLE 1

A mixture of 6.16 g of 1-chloro-4-phenyl-4-phenylsulfonylbutane, 4.25 g of 1-phenylpiperazine, 3.5 of sodium carbonate and 80 ml of dimethylformamide was refluxed with stirring for 23 hours. After cooling, water was added to the reaction mixture. The resulting mixture was extracted with chloroform, and the extract was washed with a 10% aqueous hydrochloric acid solution and with an aqueous potassium carbonate solution. To the organic layer was added 1.8 g of oxalic acid. The resulting oxalate was purified with 60% ethanol to give 6 g of 1-(4-phenyl-4-phenylsulfonylbutyl)-4-phenylpiperazine oxalate as white crystals, melting at 179°–181° C with decomposition.

EXAMPLE 2

A mixture of 6.16 g of 1-chloro-4-phenyl-4-phenylsulfonylbutane, 4.72 g of 1-(m-chlorophenyl)piperazine, 4.24 g of sodium carbonate and 80 ml of toluene was refluxed with stirring for 48 hours. Water was added to the reaction mixture, and the whole mixture was extracted with toluene. To the extract was added 1.8 g of oxalic acid. The resulting oxalate was purified with a mixture of methanol and water to give 6 g of 1-(4-phenyl-4-phenylsulfonylbutyl)-4-(m-chlorophenyl)piperazine oxalate as white crystals, melting at 170°–180° C. The corresponding dihydrochloride melts at 168°–171° C with decomposition.

EXAMPLE 3

A mixture of 6.16 g of 1-chloro-4-phenyl-4-phenylsulfonylbutane, 4.25 g of 4-(4-pyridylmethyl)piperazine, 4.24 g of sodium carbonate and 80 ml of toluene was refluxed with stirring for 72 hours. After cooling, water was added to the reaction mixture and the toluene layer was separated. The eoluene layer was extracted with a 10% aqueous hydrochloric acid solution and neutralized with potassium carbonate and then extracted with ethyl acetate. After drying over potassium carbonate, to the extract was added 7.0 g of maleic acid. The resulting maleate was purified with 2-propanol to give 3 g of 1-(4-phenyl-4-phenylsulfonylbutyl)-4-(4-pyridylmethyl)piperazine trimaleate, melting at 144°–146° C with decomposition.

Using the procedure set forth in the above examples, but substituting equivalent amounts of appropriate starting materials, the following compounds are also produced:

(1) 1-(4-phenyl-4-phenylsulfonylbutyl)-4-(mtolyl)piperazine oxalate, melting at 163°–165° C with decomposition;

(2) 1-(4-phenyl-4-phenylsulfonylbutyl)-4-(p-methoxyphenyl)piperazine oxalate, melting at 185°–187° C with decomposition;

(3) 1-(4-phenyl-4-phenylsulfonylbutyl)-4-(o-chlorophenyl)piperazine oxalate, melting at 173°–175° C with decomposition;

(4) 1-(4-phenyl-4-phenylsulfonylbutyl)-4-(p-chlorobenzyl)piperazine dimaleate, melting at 168°–171° C with decomposition;

(5) 1-[4-(p-chlorophenyl)sulfonyl-4-phenylbutyl]-4-phenylpiperazine oxalate, melting at 169°–171° C with decomposition;

(6) 1-[4-(p-chlorophenyl)-4-phenylsulfonylbutyl]-4-phenylpiperazine oxalate, melting at 150°–152° C with decomposition;

(7) 1-(4-phenyl-4-phenylsulfonylbutyl)-4-(o-ethylphenyl)piperazine oxalate, melting at 205°–208° C with decomposition;

(8) 1-(4-phenyl-4-phenylsulfonylbutyl)-4-methylpiperazine dimaleate, melting at 181°–183° C with decomposition;

(9) 1-(4-phenyl-4-phenylsulfonylbutyl)-4-(2-hydroxyethyl)piperazine dimaleate, melting at 143°–145° C with decomposition;

(10) 1-(4-phenyl-4-phenylsulfonylbutyl)-4-[2-(4-pyridyl)ethyl]piperazine trimaleate, melting at 138°–140° C with decomposition;

(11) 1-(4-phenyl-4-phenylsulfonylbutyl)-4-(2-thienylmethyl)piperazine dimaleate, melting at 178°–180° C with decomposition;

(12) 1-(4-phenyl-4-phenylsulfonylbutyl)-4-(2-pyrimidinyl)piperazine oxalate, melting at 224°–226° C with decomposition;

(13) 1-[4-(o-chlorophenyl)-4-phenylsulfonylbutyl]-4-phenylpiperazine, pale yellow oil;

(14) 1-[3-(p-methoxyphenyl)-3-phenylsulfonylpropyl]-4-phenylpiperazine, pale yellow oil;

(15) 1-(4-phenyl-4-tosylbutyl)-4-phenylpiperazine, pale yellow oil;

(16) 1-(4-phenyl-4-phenylsulfonylbutyl)-4-(m-trifluoromethylphenyl)-piperazine oxalate, melting at 149°–151° C with decomposition.

What is claimed is:

1. A piperazine compound of the formula:

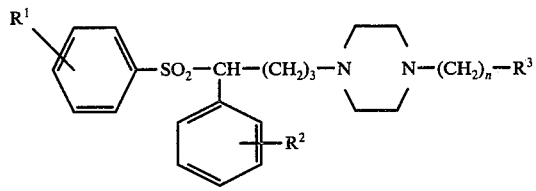

or a pharmaceutically acceptable acid addition salt thereof, wherein each of $R^1$ and $R^2$ is a hydrogen atom, a halogen atom, an alkyl group having 1 to 4 carbon atoms, an alkoxy group having 1 to 4 carbon atoms or a trifluoromethyl group; $R^3$ is an unsubstituted phenyl group or a phenyl group substituted by a halogen atom, an alkyl group having 1 to 4 carbon atoms, an alkoxy group having 1 to 4 carbon atoms or a trifluoromethyl group; and $n$ is 0, 1 or 2.

2. A compound of claim 1:

1-(4-phenyl-4-phenylsulfonylbutyl)-4-phenylpiperazine.

3. A compound of claim 1:
1-(4-phenyl-4-phenylsulfonylbutyl)-4-(m-tolyl)piperazine.

4. A compound of claim 1:
1-(4-phenyl-4-phenylsulfonylbutyl)-4-(o-chlorophenyl)piperazine.

5. A compound of claim 1:
1-(4-phenyl-4-phenylsulfonylbutyl)-4-(m-chlorophenyl)piperazine.

6. A compound of claim 1:
1-(4-phenyl-4-phenylsulfonylbutyl)-4-(m-trifluoromethylphenyl)piperazine.

7. A compound of claim 1:
1-[4-(p-chlorophenyl)sulfonyl-4-phenylbutyl]-4-phenylpiperazine.

8. A compound of claim 1:
1-[4-(o-chlorophenyl)-4-phenylsulfonylbutyl]-4-phenylpiperazine.

9. A pharmaceutical composition comprising at least one compound defined in claim 1 in combination with a pharmaceutically acceptable inert carrier or adjuvant, said compound being present in an analgetically effective amount.

10. A compound of claim 1 wherein $n$ is 0.

11. A compound of claim 1 wherein $n$ is 0 and each of $R^1$ and $R^2$ is a hydrogen atom or a chlorine atom.

12. A compound of claim 1 wherein $n$ is 0, each of $R^1$ and $R^2$ is a hydrogen atom or a chlorine atom, and $R^3$ is an unsubstituted phenyl group or a phenyl group substituted by a chlorine atom, a methyl group or a trifluoromethyl group.

* * * * *